(12) United States Patent
Rosen et al.

(10) Patent No.: US 6,503,488 B1
(45) Date of Patent: Jan. 7, 2003

(54) TOPICAL COMPOSITIONS INCLUDING DEODORANT COMPOSITIONS

(75) Inventors: Steven E. Rosen, Ft. Lauderdale, FL (US); Robert Lee Brown, Irving, TX (US)

(73) Assignee: Tend Skin International, Inc., Davie, FL (US)

( * ) Notice: Subject to any disclaimer, the term of this patent is extended or adjusted under 35 U.S.C. 154(b) by 0 days.

(21) Appl. No.: 09/439,658

(22) Filed: Nov. 12, 1999

Related U.S. Application Data

(63) Continuation-in-part of application No. 09/193,492, filed on Nov. 17, 1998, now Pat. No. 5,688,495.

(51) Int. Cl.⁷ .............................. A61K 7/32; A61K 7/34; A61K 7/36; A61K 7/00; A61K 31/60
(52) U.S. Cl. .............................. 424/65; 424/66; 424/67; 424/401; 514/159; 514/165
(58) Field of Search ........................... 424/401, 65, 67, 424/66; 514/159, 165

(56) References Cited

U.S. PATENT DOCUMENTS

| | | | |
|---|---|---|---|
| 3,136,696 A | | 6/1964 | Harrison et al. |
| 4,126,681 A | * | 11/1978 | Reller .................. 424/234 |
| 4,185,100 A | | 1/1980 | Rovee et al. |
| 4,199,576 A | | 4/1980 | Reller et al. |
| 4,505,935 A | * | 3/1985 | Larsson .................. 514/779 |
| 4,665,063 A | | 5/1987 | Bar-Shalom |
| 4,908,355 A | * | 3/1990 | Gettings et al. .............. 514/63 |
| 4,946,870 A | | 8/1990 | Partain, III et al. |
| 5,034,221 A | * | 7/1991 | Rosen et al. .................. 424/73 |
| 5,204,093 A | | 4/1993 | Victor |
| 5,223,267 A | | 6/1993 | Nichols |
| 5,387,412 A | | 2/1995 | Moore |
| 5,626,856 A | * | 5/1997 | Berndt ................. 424/401 |
| 5,672,340 A | * | 9/1997 | Sun et al. .................. 424/66 |
| 5,674,912 A | | 10/1997 | Martin |
| 5,688,495 A | * | 11/1997 | Rosen et al. .................. 424/65 |
| 5,736,126 A | * | 4/1998 | Van Engelen et al. ... 424/78.02 |
| 5,747,021 A | * | 5/1998 | McKenzie et al. ............ 424/73 |
| 5,750,093 A | * | 5/1998 | Menon et al. ................ 424/59 |
| 5,788,956 A | * | 8/1998 | De Lacharriere et al. ..... 424/65 |
| 5,824,666 A | * | 10/1998 | Deckner et al. ............ 514/152 |
| 5,948,416 A | * | 9/1999 | Wagner et al. .............. 424/401 |
| 6,001,340 A | * | 12/1999 | Rosen et al. .................. 424/73 |
| 6,010,716 A | * | 1/2000 | Saunal et al. ................ 424/449 |
| 6,156,299 A | * | 12/2000 | Rosen et al. .................. 424/73 |

OTHER PUBLICATIONS

PCT/US99/27172 International Search Report mailed Feb. 14, 2000.

* cited by examiner

Primary Examiner—Jose' G. Dees
Assistant Examiner—Marina Lamm
(74) Attorney, Agent, or Firm—Needle & Rosenberg, P.C.

(57) ABSTRACT

A topical composition for use in a variety of environments includes an active component, e.g., acetylsalicylic acid, a solvent mixture for the active components and, optionally, a silicone additive. The topical compositions according to the invention include nail hardeners, deodorants and sunscreen products.

16 Claims, No Drawings

TOPICAL COMPOSITIONS INCLUDING DEODORANT COMPOSITIONS

CROSS-REFERENCE TO RELATED APPLICATIONS

This is a continuation-in-part (CIP) application of application Ser. No. 09/193,492 filed Nov. 17, 1998 which is related to U.S. Pat. No. 5,688,495, issued Nov. 18, 1997, which is incorporated by reference in its entirety.

This application is also related to co-pending U.S. application Ser. No. 08/039,843 filed Mar. 30, 1993 for "Topical Compositions and Methods for Treating Psuedofolliculitis Barbae," which is also incorporated by reference in its entirety.

BACKGROUND OF THE INVENTION

The present invention relates to topical compositions that include acetylsalicylic acid. Examples of topical compositions according to this invention include deodorants, sunscreens and nail hardeners.

Antiperspirant and deodorant formulations typically rely on the use of alum, aluminum zirconium tetrachlorohdrexgly, and aluminum chlorohydrate as the active ingredients. Although aluminum chlorohydrate based products can be highly effective, some people are concerned that with daily use, the aluminum chlorohydrate is absorbed into the body, which might be detrimental to health. The aluminum-based compounds may react in the body in undesired ways.

Other topical compositions suffer from similar problems. For example, fingernail faces and polishes have the unfortunate effect of drying, yellowing and making the fingernails brittle, split and cracked. Typical techniques for dealing with unattractive and weak fingernails have involved either covering the problem nails, e.g., by applying acrylic to the nails and shaping them, or attempting to supply desired components, e.g., vitamins, moistening oils, minerals and the like, to the nails by applying nail polishes and/or hardeners containing such ingredients. The former solution, however, is relatively costly, employs strong smelling chemicals, and must be refilled in near the cuticle as the nail grows out. The latter, on the other hand, solution has failed to adequately improve the condition of the fingernail. Thus, the need still exists for an improved composition for hardening problem fingernails.

Sun-tanning products are well known in the art. Such products seek to minimize the damaging effects of sunlight on skin through the use of sunscreen formulations. These formulations which are generally based on an oil-in-water or water-in-oil emulsion system, suffer from a variety of disadvantages such as inefficient U.V. protection, chemical and physical instability, as well as unattractive aesthetic properties when applied to the skin. Thus, the art continues to seek to provide improved sunscreen formulations.

SUMMARY OF THE INVENTION

Among other aspects, the present invention is based upon the surprising discovery that acetylsalicylic acid-containing compositions according to the invention are capable of being used as topical formulations for a variety of purposes. In particular, the topical compositions according to the present invention can be effectively employed in deodorant, nail hardening, and sunscreen/sunblock environments.

In one aspect, the present invention relates to a topical composition comprising an active component which is acetylsalicylic acid, a solvent mixture comprising propylene glycol, glycerine, isopropyl alcohol and optionally, alcohols such as ethanol, and/or water, and at least one silicone additive.

In another aspect, the invention relates to deodorants, nail hardeners, and sunscreen products that employ acetylsalicylic acid as an active component in a solvent mixture.

These and other aspects of the invention will become apparent to those skilled in the art in light of the specification and claims that follow.

DETAILED DESCRIPTION OF THE PREFERRED EMBODIMENT

As discussed above, topical compositions according to the present invention include an active component in a solvent mixture.

The key ingredient in the active component is acetylsalicylic acid. Acetylsalicylic acid is well recognized in the art. It is widely available commercially and, thus, will not be described in detail here.

The acetylsalicylic acid is employed in a solvent mixture preferably includes the following components:

Propylene glycol (1,2-propanediol; methylene glycol) is a moisturizer and produces a pleasant emollient feel when applied to the skin. Propylene glycol has the additional benefit of being a mild germicide. However, in excessive concentrations the germicidal properties can irritate sensitive facial skin.

Glycerine (glycerol; 1,2,3-propanetriol) is a mild astringent that causes increased blood flow to the skin and allows the propylene glycol to carry the acetylsalicylic acid into the epidermis and hair follicles. Excessive amounts of glycerine could allow the propylene glycol to penetrate below the epidermis, which would be undesirable.

Isopropyl alcohol (isopropanol; 2-propanol) serves as a bulk solvent for the other ingredients of the composition. Isopropyl alcohol also serves to dissolve oils and grease thus cleaning the skin and permitting more intimate contact of the other ingredients with the skin. Isopropyl alcohol is less dehydrating to the skin than ethanol, and because it is less polar, it is a better solvent for the acetylsalicylic acid. It is anticipated, however, that ethanol in the composition would not adversely effect the effectiveness of the composition.

Other suitable solvents for use in the solvent mixture are alcohols and denatured alcohols, including ethanol; polyethylene glycols; as well as water.

Each of the components, e.g., acetylsalicylic acid, propylene glycol, glycerin, and isopropyl alcohol, ethanol, and the like are generally recognized as safe for topical application to the skin or for cosmetic purposes.

The solvent mixture preferable comprises propylene glycol in the range of about 5–15% by volume glycerine in the range of 1–10% by volume, and the balance of the mixture being made up by one or more of isopropyl alcohol, ethanol, or water. In particular, it is preferred that the balance of the solvent mixture comprises at least 50% by volume of isopropyl alcohol. The only requirement for the solvent mixture is that the polarity of the resulting composition not be so high such that the acetylsalicylic acid will readily precipitate from the solution at ordinary room temperatures. More preferably, the acetylsalicylic acid should not precipitate at temperatures above 50° F.

More preferred embodiments of the invention employ propylene glycol in an amount of about 10–15% by volume, glycerine in an amount of about 2–4% by volume with the balance of the solvent mixture being made up of isopropyl alcohol alone or a solution of isopropyl alcohol and ethanol and/or water provided that the isopropyl alcohol is at least 7% by volume of the solution.

The acetylsalicylic acid is preferably introduced into the solvent mixture. To this end, the acetylsalicylic acid is preferably present in an amount between 5% by weight per volume of the solvent mixture up to saturation in the solvent mixture. More preferably, the acetylsalicylic acid is present in an amount of about 10% by volume of the mixture up to 18% by weight per unit volume of the mixture with about 15%–18% being even more preferred.

In one embodiment topical compositions according to the invention further includes one or more silicone additives. Silicone additives which can be employed in the inventive compositions include siloxanes, polysiloxanes, or mixtures thereof. Specific examples of suitable materials include decamethylcyclopentasiloxane, octamethylcyclotetrasiloxane and dimethicone. To this end a variety of siloxanes and polysiloxanes are commercially available. One example of a commercially available silicone for use in the invention is cyclomethicone such as that available from Dow Coming as Dow Coming 245 Fluid No. 540.

The amount of this optional silicone additive is dependent upon the combination of desired properties for the resulting composition. For example, the introduction of silicone additive into the composition is capable of improving one or more of the following properties:

(1) Shelf life. In particular the introduction of silicone is capable of increasing the shelf life for the composition under standard room wide conditions for up to two months or more;

(2) Skin Feel. In this regard, the drying and/or peeling of the skin is decreased. Moreover, the composition can provide an improved "feel" upon use, i. e., less stinging and burning particularly after hair removal procedures.

(3) Product Strength. An enhanced strength of the product in so far as the silicone facilitates contact between the active component and the skin surface.

The silicone additive is preferably introduced in an amount such that the volume ratio of silicone additives to the active material/solvent mixture combination is 20:1–1:20. The more preferred ratio is dependent on the particular environment of use. For example, one environment where the composition coating silicone additive can find particular utility is as a nail-hardening agent. In this environment, a volume ratio of 14:1–20:1 of silicone component to active/solvent mixture is preferred. In deodorant compositions, a volume ratio of about 2:1 to about 5:1, preferably about 3:1 to about 4:1, of silicone compound to active/solvent mixture is preferred.

The inventive composition, with or without the silicone component, can be employed in environments including:
1. clearing up acne;
2. treating topical viral and fungal infections, e.g., topical cold sores (herpes virus), white spots after sun-tanning (fungus), athletes foot, warts (regular application reduces warts significantly in 7–10 days), and ringworm infections;
3. treating most vesicle producing skin disorders;
4. preventing bug bites;
5. treating bug bites, e.g., reducing stinging;
6. acting as drawing salve, e.g., helps drain infections on skin;
7. styptic effect, e.g., stops bleeding from small cuts;
8. wound closure, e.g., helps close wound edges;
9. soothing first and second degree burns and aids healing;
10. shrinking scar tissue;
11. shrinking stretch marks;
12. acting as a skin barrier, i. e., can minimize or even prevent uptake of chemicals by the skin. For example, can prevent indoor sun tanning products from reaching the skin for at least a week after application of the formula;
13. skin cleansing, including removing inks and other stains from skin;
14. treating salt air sting, e.g., can prevent stinging from salt air at the beach on legs, etc. that were just shaved;
15. helping "work out" splinters from wood slivers, e.g., can aid in removing "hair splinters" from under fingernails of barbers, hair stylists, and waxing technicians;
16. treating itching from various disorders, such as Pityriasis Rosea;
17. drawing out "ingrown" finger and toe nails;
18. shrinking some skin cancers, such as Basal Cell Carcinoma; and
19. acting as exfoliant, e.g., causes slight skin peeling which smoothes skin.

The preferred environments include nail hardeners, deodorant, and sunscreen protection.

To this end, the amount of active compound can be optimized for use in the desired environment. Moreover, the foregoing compositions can include one or more additives appropriate for its ultimate end use. For example, in deodorant compositions, a waxy carrier additive can be employed. However, it should be noted that such components are optional. For example, in certain deodorant environments, such as foot deodorants, a waxy carrier is not typically employed.

In this deodorant environment, any waxy carrier recognized for use in deodorant compositions can be employed in the present invention. Specific examples of suitable materials include fatty alcohols such as cetyl alcohol (1-hexadecanol), stearyl alcohol and the like. Additional examples of suitable materials include sodium stearate, stearic acid, and hydrogenated castor oil.

In this aspect of the invention, acetylsalicylic acid is preferably present in the range of up to about 40–50% by weight per trait volume of the solvent mixture up to saturation of the solvent mixture and the solvent mixture comprises propylene glycol in about 10% by volume, glycerine in about 2 percent by volume, and the balance of the volume substantially made up with isopropyl alcohol alone or a solution of isopropyl alcohol and water, provided that the isopropyl alcohol is at least about 70% by volume of the solution of isopropyl alcohol and water. Where the isopropyl alcohol is about 70% by volume of the solution of isopropyl alcohol and water, the saturation concentration of the acetylsalicylic acid in this solvent mixture is about 18% by weight per unit volume.

In preparing the composition, it can be helpful to gently warm while stirring the solvent mixture to assist the acetylsalicylic acid in completely dissolving in the solvent mixture. It has been observed that the typical consumer tends to prefer a product that is homogeneous in appearance and without any visable precipitate. The acetylsalicylic acid is virtually insoluble in water or water based substances. Thus, aloe vera, for example, while it is soothing to the skin, tends to quickly hydrolyze acetylsalicylic acid. The hydrolysis of the acetylsalicylic acid would substantially and undesirably shorten the shelf life of the product.

After the acetylsalicylic acid is dissolved in the solvent mixture as just described, the acetylsalicylic acid solution is then further mixed with a waxy carrier to provide a deodorant composition. According to this aspect of the invention, the waxy carrier can be (a) either cetyl alcohol or stearyl alcohol and/or (b) either sodium stearate or stearic acid. Thus, the composition provides an appropriate deodorant delivery system. For example, according to the one embodiment of the invention, 25–30 fl. ounces of the acetylsalicylic acid/solvent mixture is then mixed with 30–35 ounces of (a) and 0–5 ounces of (b).

In addition to the waxy materials, other additives can be included. One additional additive includes Potassium Hexadecyl Hydrogen Phosphate such as that sold under the Monofax Map160K tradename which is preferably added in an amount of 1–5 wt %. Examples of other additives include castor oils and particular hydrogenated castor oils such as 600° C. hydrogenated castor oils, and non-aluminum metal-based compounds such as zirconium hydroxychloride and titanium dioxide. These materials are preferably present in the following amounts:

| | |
|---|---|
| Hydrogenated Castor Oil | 5–35%, preferably 10–25%, more preferably 10–15% |
| Zirconium Hydroxychloride | 1–20%, preferably 1–10%, more preferably 1–5% |
| Titanium Dioxide | 2–15% |

A specific example of a suitable deodorant composition includes:

| INGREDIENT | QUANTITY/10 GALS |
|---|---|
| 1. Cyclomethicone | 500–600 Fluid Ounces |
| 2. Stearyl Alcohol | 200–250 Ounces (wt.) |
| 3. Hydrogenated Castor Oil | 100–150 Ounces (wt.) |
| 4. Acetysalicylic Acid Solution | 150–200 Fluid Ounces |
| 5. Zirconium Hydroxychloride | 200–250 Fluid Ounces |
| 6. Potassium Hexadecyl Hydrogen Phosphate | 0–50 Ounces (wt.) |

In addition, an effective amount of a coloring agent such as FD&C Blue No. 6 can be added to the composition to effect a pleasing color to the product. Furthermore, fragrance such as citrus or other perfume is also added to create a pleasant smell, which can help mask undesired body odor. These materials can be introduced together with, or separately from the waxy carrier in producing the deodorant composition.

The deodorant compositions according to the invention have a waxy consistency, and with sufficient proportion of waxy carrier can be formed into a stick for convenient application to the skin.

Another topical composition according to the invention is a sunscreen composition. While the acetylsalicylic acid can be a sun screen/block agent, it is preferred that one or more additional sunscreen agents are included with the active composition/solvent mixture.

A wide variety of sunscreen agents are useful herein. These sunscreen agents include organic compounds and their salts as well as inorganic particulate materials. Without being limited by theory, it is believed that sunscreen agents provide protection from ultraviolet radiation by one or more of the following mechanisms including absorption, scattering, and reflection of the ultraviolet radiation.

The sunscreen agent used in this invention is preferably at least one compound capable of absorbing ultraviolet light in the erythemal range of about 280 to about 320 nanometers and which are safe for use on human skin. Examples of such ultraviolet light absorbing compounds include p-aminobenzoates, p-dialkylaminobenzoates, salicylates, cinnamates, benzophenones, and acetophenones. Examples of specific ultraviolet light absorbing compounds include benzophenone-3, p-aminobenzoic acid, 2-ethyoxyethyl p-methoxycinnamate, diethanolamine p-methoxycinnamate, digalloyl trioleate, 2,2'dihydroxy-4methoxybenzophenone, ethylhexyl p-methoxycinnamage, 2-ethylhexyl salicylate and the like.

Compounds which absorb ultraviolet radiation having wavelengths above 320 nanometers can be added to prevent sunburn potentiality effects or to help protect people who are photosensitized to long ultraviolet radiation.

Non-limiting examples of suitable sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; U.S. Pat. No. 5,170,731, to Sabatelli et al., issued Nov. 3, 1992; U.S. Pat. No. 5,138,089, to Sabatelli, issued Aug. 11, 1992; U.S. Pat. No. 5,041,282, to Sabatelli, issued Aug. 20,1991; U.S. Pat. No 4,999,186, to Sabatelli et al., issued Mar. 12, 1991; U.S. Pat. No. 4,937, 370, to Sabatelli, issued Jun. 26, 1990; and Segarin, et al., at Chapter VIII, pages 189 et seq., of Cosmetics Science and Technology; all of these documents being incorporated herein by reference in their entirety.

Specific examples of suitable sunscreen agents include 2-ethylhexyl p-methoxycinnamate, octyl salicylate, octocrylene, oxybenzone, 2-ethylhexyl N, N-dimethylaminobenzoate, p-aminobenzoic acid, 2-phenylbenzirnidazole-5-sulfonic acid, homomenthyl salicylate. DEA p-methoxcinnamate, 4,4'methoxy-tbutyldibenzoylmethane, 4-isopropyldibenzoylmethane, 3-(4-methylbenzylidene) camphor, 3-benzylidene camphor, 4-N,N-dimethylaminobenzoic acid ester with 2,4-dihydroxybenzophenone, 4-N,N-dimethylaminobenzoic acid ester with 2-hydroxy-4-(2-hydroxyethoxy) benzophenone, 4-N,N-dimenthylaminobenzoic acid ester with 4-hydroxydibenzoyl-methane, 4-N,N-dimethylaminobenzoic acid ester with 4-(2-hydroxyethoxy) dibenzoynethane, 4-N,N-di(2-ethylhexyl)-arninobenzoic acid ester with 2,4-dihydroxybenzophenone, 4-N,N-di(2-thylhexyl)aminobenzoic acid ester with 2-hydroxy-4(2-hydroxyethoxy)benzophenone, 4-NN-di(2-ethylhexyl) aminobenzoic acid ester with 4-hydroxydibenzoylmethane, 4-NN-N,N-di(2-ethylhexyl)aminobenzoic acid ester with 4-(2-hydroxyethoxy) dibenzoylmethane, 4-N,N-(2-ethylhexyl)methylaminobenzoic acid ester with 2,4-dihydroxybenzophenone, 4-N,N-(2-ethylhexyl)methylaminobenzoic acid ester with 2-hydroxy-4-(2-hydroxyethoxy)benzophenone, 4-N,N-(2-ethylhexyl) methylaminobenzoic acid ester with 4-hydroxydibenzoylmethane, 4-N,N-(2-ethylhexyl)methylaminobenzoic acid ester with 4-(2-hydroxyethoxy)dibenzoylmethane titanium dioxide, zinc oxide, iron oxide, and mixtures thereof.

The total amount of the sunscreen agent(s) (including acetylsalcylic acid) will vary depending upon the additional sunscreen or sunscreens chosen and the desired Sun Protection Factor (SPF) to be achieved, SPF is a commonly used measure of photoprotection of a sunscreen against erythema. The SPF is defined as the ratio of the ultraviolet energy required to produce minimal erythema on protected skin to that required to produce the same minimal erythema on unprotected skin in the same individual. See Federal Register. Vol. 43, No. 166, pp. 38206–38269, Aug. 25, 1978, which is incorporated herein by reference in its entirety. Typical SPF range from 2 to 45 or even higher.

The topical composition according to this invention can also be in the form of a nail hardener. While the silicone component containing composition is itself suitable for use as a nail hardener, additives such as vitamins, moisturizing oils, minerals and nutrients can also be included. These additives are individually recognized in the art.

For example, U.S. Pat. No. 4,708,866 to Turco et al. discloses an artificial nail forming composition to shape the fingernails having calcium, vitamins A, B, C and E and other ingredients in a base of mono- and poly-alkyl methacrylate. U.S. Pat. No. 4,363,796 to Bouillon and U.S. Pat. No. 4,919,920 to Devos and U.S. Pat. Nos. 3,877,702 and 3,928,561 to Baldwin disclose fingernail-hardening compositions with vitamins and other ingredients. U.S. Pat. No. 5,210,133 to O'Lenick, Jr. refers to vitamins being useful for fingernails. These patents are incorporated by reference in their entirety.

The topical compositions of the present invention can comprise a wide range of additional components. These additional components should be pharmaceutically acceptable. The CTFA *Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, absorbents, anti-acne agents, anticaking agents, antifoaming agents, antimicrobial agents, antiolidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, skin conditioning agents (humectants, miscellaneous, and occlusive), slip agents, thickeners and viscosity enhancing agents. Specific examples of suitable additive include viscosity enhancing agents such as Carbomers and slip enhancing agents, e.g., polyethylene glycols such as PEG-8.

While the present invention has been described in terms of certain preferred embodiments thereof, it should be understood that various modifications, substitutions, omissions and other changes will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A topical composition for use as a deodorant, comprising:
    a) an active deodorizing component comprising (i) a solvent carrier, wherein the solvent carrier comprises at least one pharmaceutically acceptable solvent selected from among propylene glycol, glycerine, isopropyl alcohol, ethanol and water; and (ii) acetylsalicylic acid, wherein the acetylsalicylic acid is present in an amount not exceeding about 18% by weight per unit volume of the solvent carrier;
    b) a moisture barrier component comprising at least one aluminum free compound suitable for use in a deodorant composition; and
    c) at least one silicone additive; wherein the acetylsalicylic acid of a) is present in an amount effective to provide a deodorant function for the composition and, wherein component b) is present in an amount effective to provide a moisture barrier function for the composition.

2. The composition of claim 1, wherein the solvent carrier of a) comprises:
    i) 5%–15% by volume of propylene glycol;
    ii) 1%–10% by volume of glycerine;
    iii) 75%–94% by volume of a solvent mixture comprising isopropyl alcohol.

3. The composition of claim 2, wherein the solvent carrier of (a) further comprises ethanol, water, or a combination thereof.

4. The composition of claim 2, wherein the solvent carrier of (a) comprises at least 7% by volume of isopropyl alcohol.

5. The composition of claim 1, wherein the silicone additive comprises a siloxane, polysiloxane, or a combination thereof.

6. The composition of claim 1, wherein the silicone additive comprises decamethylcyclopentasiloxane, octomethylcyclotetrasiloxane, dimethicone, or a combination thereof.

7. The composition of claim 1, wherein the silicone additive comprises cyclomethicone, dimethicone, or a combination thereof.

8. The composition of claim 1, wherein the ratio of amount of silicone additive to amount of active deodorizing component is about 2:1 to about 5:1.

9. The composition of claim 1, wherein the ratio of amount of silicone additive to amount of active deodorizing component is about 3:1 to about 4:1.

10. The composition of claim 1, further comprising a waxy carrier.

11. The composition of claim 10, wherein the waxy carrier is selected from the group consisting of cetyl alcohol, stearyl alcohol, sodium stearate, stearic acid, and mixtures thereof.

12. The composition of claim 10, wherein the waxy carrier is present in an amount of about 20% to about 80% by weight of the composition.

13. The composition of claim 1, wherein the at least one aluminum free compound comprises zirconium hydroxy chloride.

14. The composition of claim 1, further comprising an effective amount of a coloring agent to change the appearance of the composition.

15. The composition of claim 1, further comprising an effective amount of a fragrance to provide a pleasant smell to the composition.

16. The composition of claim 10, wherein the waxy carrier comprises hydrogenated castor oil.

* * * * *